(12) United States Patent
Huang et al.

(10) Patent No.: US 11,410,302 B2
(45) Date of Patent: Aug. 9, 2022

(54) TWO AND A HALF DIMENSIONAL CONVOLUTIONAL NEURAL NETWORK FOR PREDICTING HEMATOMA EXPANSION IN NON-CONTRAST HEAD COMPUTERIZED TOMOGRAPHY IMAGES

(71) Applicant: TENCENT AMERICA LLC, Palo Alto, CA (US)

(72) Inventors: Chao Huang, Palo Alto, CA (US); Zhen Qian, Santa Clara, CA (US); Hui Tang, Mountain View, CA (US); Yusheng Xie, Mountain View, CA (US); Shihyao Lin, Palo Alto, CA (US); Kun Wang, San Jose, CA (US); Xiaozhong Chen, Cedarburg, WI (US); Lianyi Han, Palo Alto, CA (US); Zhimin Huo, Palo Alto, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 74 days.

(21) Appl. No.: 16/670,133

(22) Filed: Oct. 31, 2019

(65) Prior Publication Data
US 2021/0133957 A1     May 6, 2021

(51) Int. Cl.
*G06T 7/00*     (2017.01)
*G06T 7/11*     (2017.01)
(Continued)

(52) U.S. Cl.
CPC ............. *G06T 7/0012* (2013.01); *A61B 6/032* (2013.01); *A61B 6/469* (2013.01); *A61B 6/501* (2013.01);
(Continued)

(58) Field of Classification Search
CPC .. G06T 7/0012; G06T 7/62; G06T 7/11; G06T 2207/10081; G06T 2207/10088;
(Continued)

(56) References Cited

U.S. PATENT DOCUMENTS

| | | |
|---|---|---|
| 2011/0040168 A1* | 2/2011 | Arnaud ................ G06T 7/0012 600/407 |
| 2012/0184840 A1 | 7/2012 | Najarian et al. |

(Continued)

OTHER PUBLICATIONS

Olli Oman et al., "3D convolutional neural networks applied to CT angiography in the detection of acute ischemic stroke" European Radiology Experimental, vol. 3, No. 8, 2019, (11 pages total).

(Continued)

*Primary Examiner* — Vu Le
*Assistant Examiner* — Julius Chai
(74) *Attorney, Agent, or Firm* — Sughrue Mion, PLLC

(57) ABSTRACT

A method and apparatus include receiving a three dimensional (3D) non-contrast computed tomography (NCCT) image of a head including a hematoma. A plurality of two dimensional (2D) images of the head including the hematoma are generated using the 3D NCCT image of the head including the hematoma. A plurality of 2D hematoma images are generated using a first 2D convolutional neural network (CNN) based on the plurality of 2D images. A 3D region of interest (ROI) that encompasses the hematoma is identified based on the plurality of 2D hematoma images. A plurality of 2D images that correspond to the ROI are generated. A hematoma expansion (HE) prediction score is determined using a second CNN based on the plurality of 2D images that correspond to the ROI. The HE prediction score is provided.

16 Claims, 5 Drawing Sheets

(51) Int. Cl.
*G06T 7/62* (2017.01)
*A61B 6/03* (2006.01)
*A61B 6/00* (2006.01)
*G06V 10/25* (2022.01)

(52) U.S. Cl.
CPC .......... *A61B 6/5217* (2013.01); *A61B 6/5223* (2013.01); *G06T 7/11* (2017.01); *G06T 7/62* (2017.01); *G06V 10/25* (2022.01); *G06T 2207/10081* (2013.01); *G06T 2207/20084* (2013.01); *G06T 2207/30101* (2013.01); *G06T 2207/30196* (2013.01); *G06V 2201/03* (2022.01)

(58) Field of Classification Search
CPC . G06T 2207/20084; G06T 2207/30101; G06T 2207/30196; A61B 6/032; A61B 6/501; A61B 6/5217; A61B 6/5223; A61B 5/7267; G06K 9/3233; G06K 2209/05; G06N 3/0454; G16H 30/40
See application file for complete search history.

(56) References Cited

U.S. PATENT DOCUMENTS

| | | |
|---|---|---|
| 2015/0140127 A1 | 5/2015 | Ramirez et al. |
| 2018/0033144 A1 | 2/2018 | Risman et al. |
| 2019/0021677 A1* | 1/2019 | Grbic .................. A61B 5/7292 |
| 2019/0050992 A1* | 2/2019 | Xu ........................ G06N 3/04 |
| 2019/0313963 A1* | 10/2019 | Hillen ................ G06N 3/0454 |
| 2020/0219609 A1* | 7/2020 | Harte .................... G16H 15/00 |
| 2020/0320751 A1* | 10/2020 | Siemionow .......... A61B 6/5211 |
| 2020/0327661 A1* | 10/2020 | Oved .................... G16H 30/40 |

OTHER PUBLICATIONS

P.D. Chang et al., Hybrid 3D/2D Convolutional Neural Network for Hemorrhage Evaluation on Head CT, AJNR Am J Neuroradiol, vol. 39, Sep. 2018, pp. 1609-1616 (8 pages total).

International Search Report with Written Opinion of the International Searching Authority dated Nov. 17, 2020, in International Application No. PCT/US20/47543.

* cited by examiner

TWO AND A HALF DIMENSIONAL CONVOLUTIONAL NEURAL NETWORK FOR PREDICTING HEMATOMA EXPANSION IN NON-CONTRAST HEAD COMPUTERIZED TOMOGRAPHY IMAGES

BACKGROUND

Convolutional neural networks (CNNs) have been used in various medical imaging applications, including classification, segmentation, registration, etc. However, in most of the applications, the CNNs are based on two dimensional (2D) images because three dimensional (3D) models require substantially more computations, memory space, and training data. Further, many medical imaging modalities generate inherently 3D images, such as computed tomography (CT), magnetic resonance imaging (MRI), positron emission tomography (PET) etc. To process 3D images, many 3D CNN architectures have been proposed.

SUMMARY

According to some possible implementations, a method includes receiving a three dimensional (3D) non-contrast computed tomography (NCCT) image of a head including a hematoma; generating a plurality of two dimensional (2D) images of the head including the hematoma using the 3D NCCT image of the head including the hematoma; generating, using a first 2D convolutional neural network (CNN), a plurality of 2D hematoma images based on the plurality of 2D images; identifying a 3D region of interest (ROI) that encompasses the hematoma based on the plurality of 2D hematoma images; generating a plurality of 2D images that correspond to the ROI; determining, using a second CNN, a hematoma expansion (HE) prediction score based on the plurality of 2D images that correspond to the ROI; and providing the HE prediction score.

According to some possible implementations, a device comprises at least one memory configured to store program code; and at least one processor configured to read the program code and operate as instructed by the program code, the program code including: receiving code configured to cause the at least one processor to receive a three dimensional (3D) non-contrast computed tomography (NCCT) image of a head including a hematoma; first generating code configured to cause the at least one processor to generate a plurality of two dimensional (2D) images of the head including the hematoma using the 3D NCCT image of the head including the hematoma; second generating code configured to cause the at least one processor to generate, using a first 2D convolutional neural network (CNN), a plurality of 2D hematoma images based on the plurality of 2D images; identifying code configured to cause the at least one processor to identify a 3D region of interest (ROI) that encompasses the hematoma based on the plurality of 2D hematoma images; third generating configured to cause the at least one processor to generate a plurality of 2D images that correspond to the ROI; determining code configured to cause the at least one processor to determine, using a second CNN, a hematoma expansion (HE) prediction score based on the plurality of 2D images that correspond to the ROI; and providing code configured to cause the at least one processor to provide the HE prediction score.

According to some possible implementations, a non-transitory computer-readable medium stores instructions, the instructions comprising: one or more instructions that, when executed by one or more processors of a device, cause the one or more processors to: receive a three dimensional (3D) non-contrast computed tomography (NCCT) image of a head including a hematoma; generate a plurality of two dimensional (2D) images of the head including the hematoma using the 3D NCCT image of the head including the hematoma; generate, using a first 2D convolutional neural network (CNN), a plurality of 2D hematoma images based on the plurality of 2D images; identify a 3D region of interest (ROI) that encompasses the hematoma based on the plurality of 2D hematoma images; generate a plurality of 2D images that correspond to the ROI; determine, using a second CNN, a hematoma expansion (HE) prediction score based on the plurality of 2D images that correspond to the ROI; and provide the HE prediction score.

DETAILED DESCRIPTION

Although the models mentioned above are based on 3D CNNs, the models still suffer from computational burden and curse of dimensionality. For instance, due to limited graphics processing unit (GPU) memory, the batch size is usually set to be "1" for training 3D U-Nets or V-Nets for segmentation tasks. Those limitations restrict the applications of the 3D CNNs.

Convolutional neural networks (CNNs) have been widely used in medical imaging applications, including both 2-dimensional (2D) models and 3-dimensional (3D) models, and 2D CNNs are generally more common than 3D CNNs due to computational intensity and training data availability, However, many medical images are intrinsically 3D, such as non-contrast computed tomography (NCCT) images for intracranial hemorrhage (ICH) detection. The present disclosure provides a method to process 3D NCCT images for ICH detection and hematoma expansion (HE) prediction using 2D CNNs.

Specifically, the present disclosure applies a 2D U-Net on each 2D slice of NCCT images to segment the hematomas. Then, a fixed-size, 3D sub-volume (called "region of interest (ROI)") containing the hematomas and some surrounding context is determined from the hematoma mask, and finally each slice in the ROI is utilized as a channel of the input of a 2D classification CNN to predict HE. In this way, we circumvent the computational limitation of 3D CNNs and achieve HE prediction accuracy that is substantially similar to radiologists' performance.

Figure 1A:
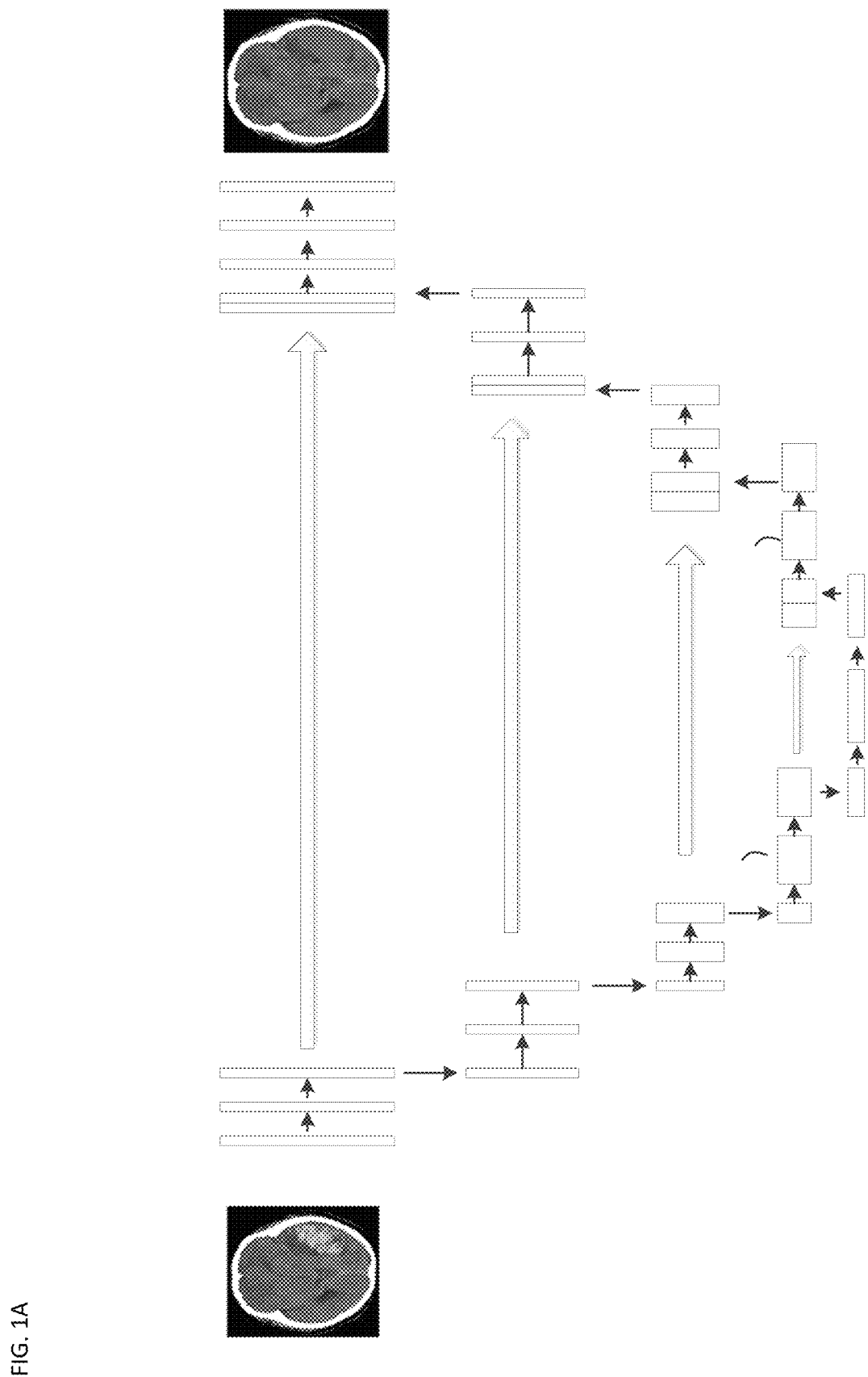
FIGS. 1A and 1B are diagrams of an overview of an example implementation described herein.
Figure 1B:
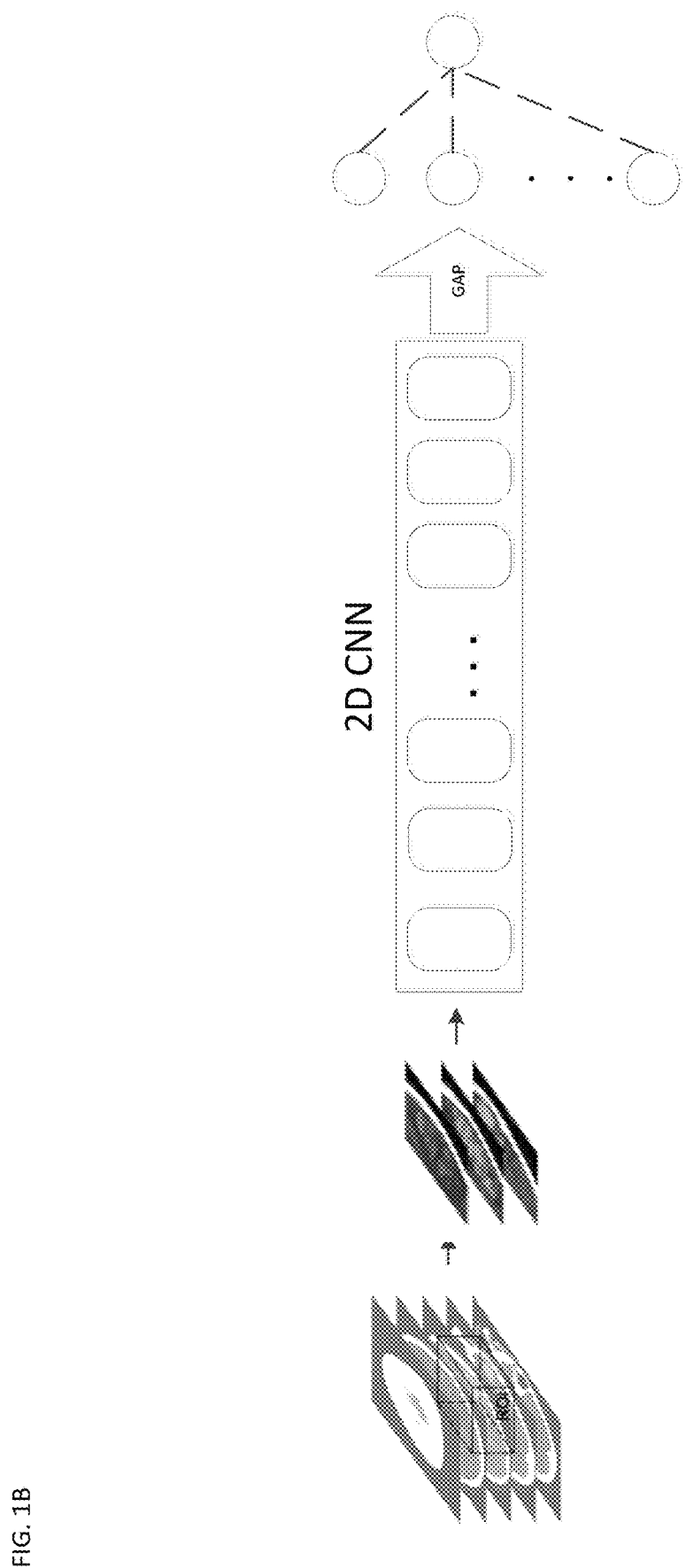

U-Net is a 2D CNN model for image segmentation, particularly for biomedical images. The present disclosure provides a technique that generates hematoma masks by utilizing U-Net to segment hematomas in NCCT images. The architecture of U-Net is shown in FIG. 1A. For example, As shown in FIG. 1B, after the hematoma masks for all slices are generated, a bounding box that contains the hematoma can be determined. The size of the bounding box depends on the volume of the hematoma, so a fixed-size sub-volume called ROI may be identified from the bounding box, such that their centers coincide and the size of the ROI can contain almost all possible hematomas (e.g., 192×192×14 ROIs for 512×512×30 NCCT images).

Once the ROI is extracted from the whole volume, each slice in the ROI is employed as a feature channel of the input to a classification CNN (e.g., a NASNet model) for 2D images to predict HEs.

The present disclosure permits the processing of 3D images, which are common for medical applications, with 2D CNNs. Further, the present disclosure improves efficiency by circumventing the intensive computations of 3D CNNs.

Figure 2:
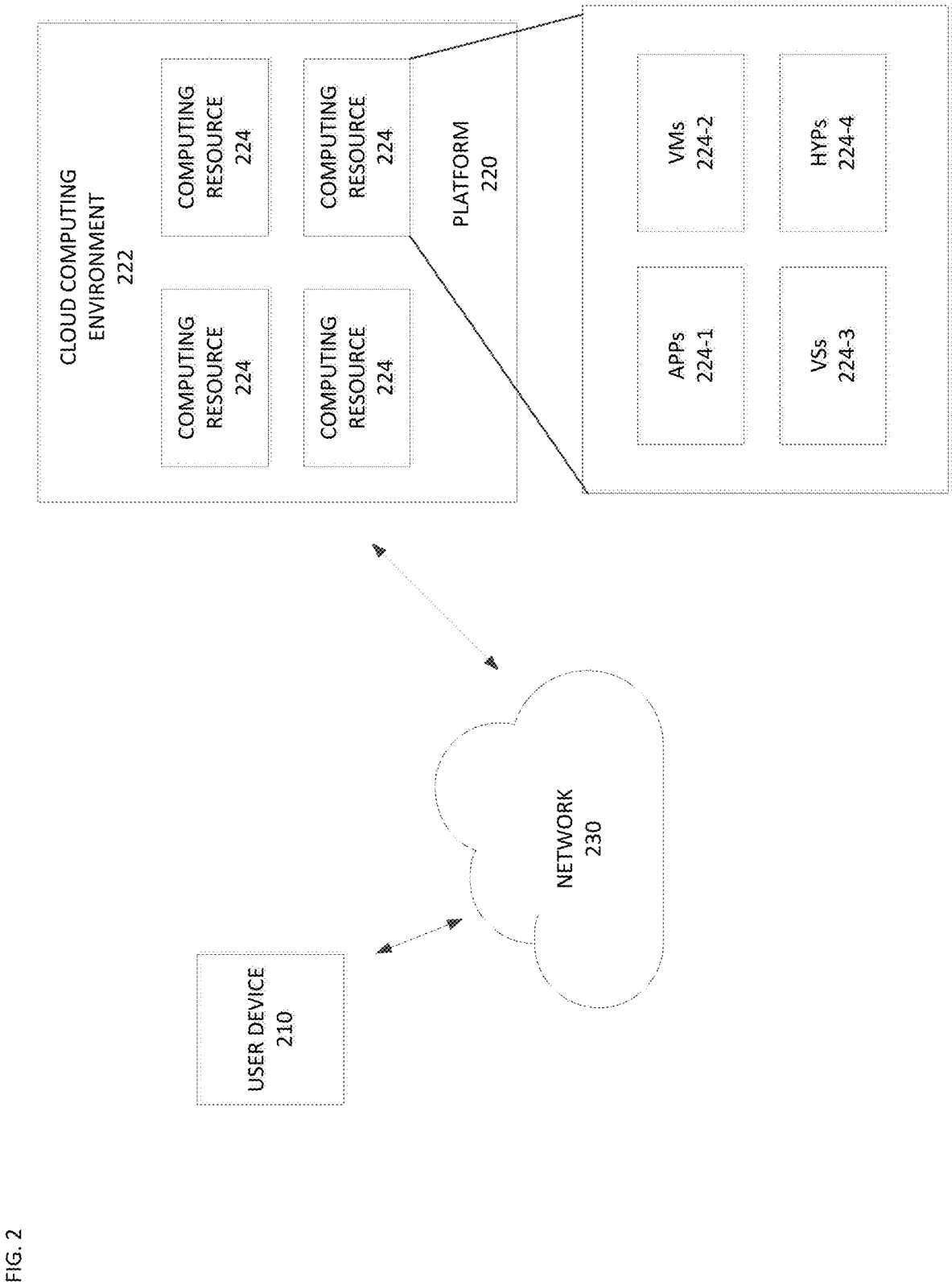
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a user device 210, a platform 220, and a network 230. Devices of environment 200 may interconnect via wired connections, wireless connections, or a combination of wired and wireless connections.

User device 210 includes one or more devices capable of receiving, generating, storing, processing, and/or providing information associated with platform 220. For example, user device 210 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 210 may receive information from and/or transmit information to platform 220.

Platform 220 includes one or more devices capable of providing a hematoma expansion prediction score using a 2.5 dimensional convolutional neural network, as described elsewhere herein. In some implementations, platform 220 may include a cloud server or a group of cloud servers. In some implementations, platform 220 may be designed to be modular such that certain software components may be swapped in or out depending on a particular need. As such, platform 220 may be easily and/or quickly reconfigured for different uses.

In some implementations, as shown, platform 220 may be hosted in cloud computing environment 222. Notably, while implementations described herein describe platform 220 as being hosted in cloud computing environment 222, in some implementations, platform 220 is not be cloud-based (i.e., may be implemented outside of a cloud computing environment) or may be partially cloud-based.

Cloud computing environment 222 includes an environment that hosts platform 220. Cloud computing environment 222 may provide computation, software, data access, storage, etc. services that do not require end-user (e.g., user device 210) knowledge of a physical location and configuration of system(s) and/or device(s) that hosts platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, or the like.

Application 224-1 includes one or more software applications that may be provided to or accessed by user device 210 and/or sensor device 220. Application 224-1 may eliminate a need to install and execute the software applications on user device 210. For example, application 224-1 may include software associated with platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program, and may support a single process. In some implementations, virtual machine 224-2 may execute on behalf of a user (e.g., user device 210), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems, and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
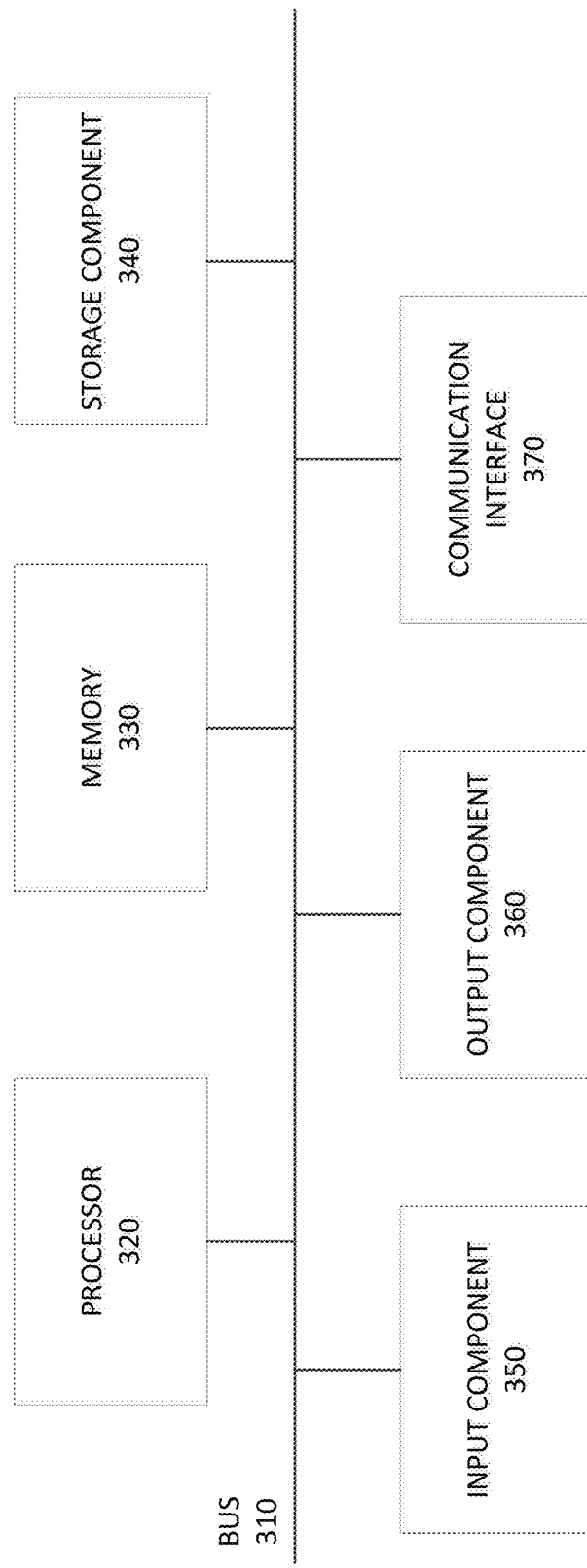
FIG. 3 is a diagram of example components of one or more devices of FIG. 2.

FIG. 3 is a diagram of example components of a device 300. Device 300 may correspond to user device 210 and/or platform 220. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
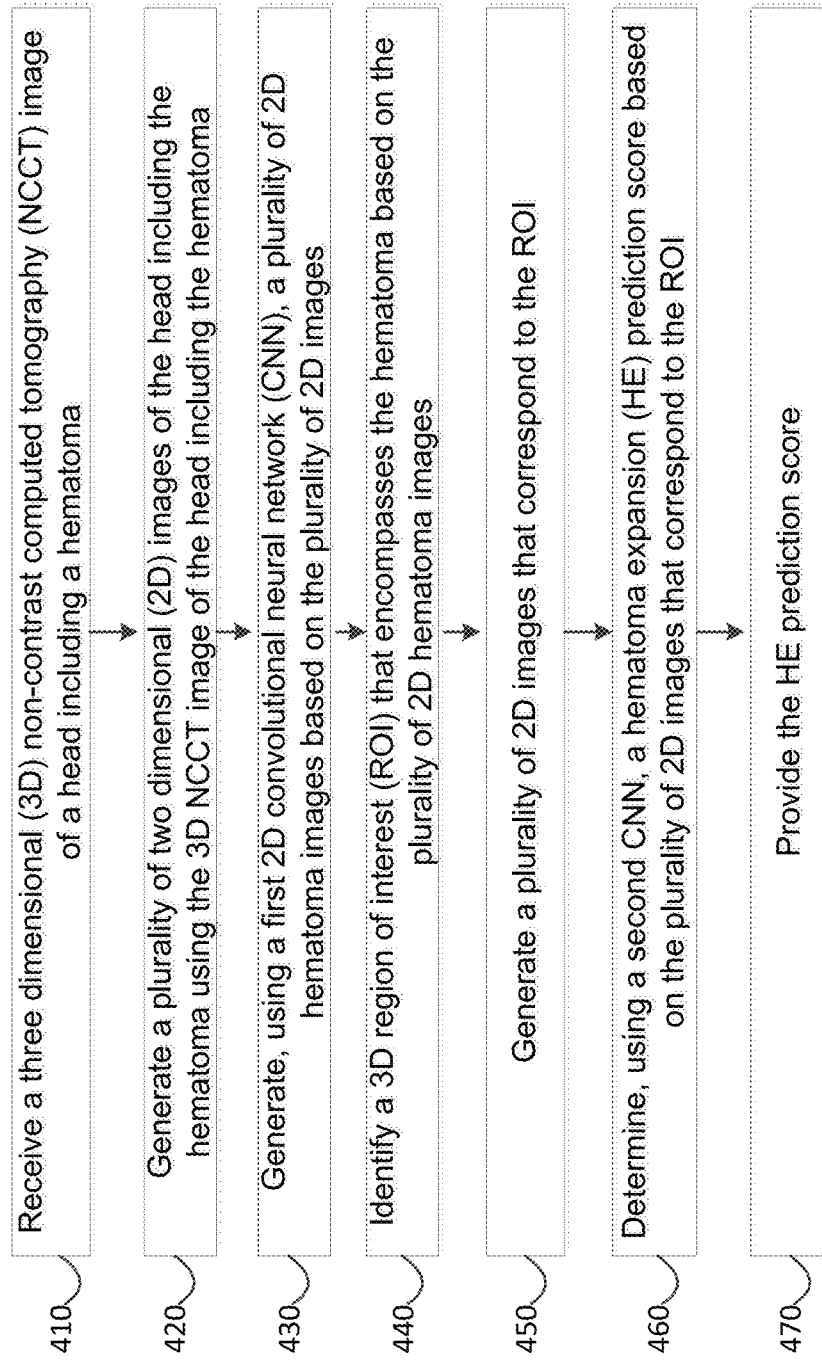
FIG. 4 is a flow chart of an example process for providing a hematoma expansion prediction score using a 2.5 dimensional convolutional neural network.

FIG. 4 is a flow chart of an example process 400 for providing a hematoma expansion prediction score using a 2.5 dimensional convolutional neural network. In some implementations, one or more process blocks of FIG. 4 may be performed by platform 220. In some implementations, one or more process blocks of FIG. 4 may be performed by another device or a group of devices separate from or including platform 220, such as user device 210.

As shown in FIG. 4, process 400 may include receiving a three dimensional (3D) non-contrast computed tomography (NCCT) image of a head including a hematoma (block 410).

As further shown in FIG. 4, process 400 may include generating a plurality of two dimensional (2D) images of the head including the hematoma using the 3D NCCT image of the head including the hematoma (block 420).

As further shown in FIG. 4, process 400 may include generating, using a first 2D convolutional neural network (CNN), a plurality of 2D hematoma images based on the plurality of 2D images (block 430).

As further shown in FIG. 4, process 400 may include identifying a 3D region of interest (ROI) that encompasses the hematoma based on the plurality of 2D hematoma images (block 440).

As further shown in FIG. 4, process 400 may include generating a plurality of 2D images that correspond to the ROI (block 450).

As further shown in FIG. 4, process 400 may include determining, using a second CNN, a hematoma expansion (HE) prediction score based on the plurality of 2D images that correspond to the ROI (block 460).

As further shown in FIG. 4, process 400 may include providing the HE prediction score (block 470).

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method comprising:
   receiving a three dimensional (3D) non-contrast computed tomography (NCCT) image of a head that includes at least one intracranial hemorrhage;
   generating a plurality of two dimensional (2D) NCCT images of the head using the 3D NCCT image of the head;
   generate, by applying a 2D U-Net convolutional neural network (CNN) on each of the plurality of 2D NCCT images, hematoma masks for the plurality of 2D NCCT hematoma images;
   determining a bounding box that contains a hematoma from the hematoma masks such that a center of the hematoma in each of the plurality of 2D NCCT hematoma images coincides,
   determining a fixed-size 3D region of interest (ROI) containing the hematoma from the bounding box;
   extracting the fixed-size 3D ROI from the 3D NCCT image;
   generating a plurality of 2D NCCT slices of the fixed-size 3D ROI that is extracted;
   predicting a hematoma expansion (HE) of the at least one intracranial hemorrhage by inputting each of the plurality of 2D NCCT slices to a 2D NASNet CNN, each of the plurality of 2D NCCT slices being a feature channel of the 2D NASNet CNN, and combining a plurality of outputs of the 2D NASNet CNN to generate an HE prediction score of the at least one intracranial hemorrhage; and
   providing the HE prediction score.

2. The method of claim 1, wherein the size of the fixed-size 3D ROI contains all hematomas in the 3D NCCT image of the head.

3. The method of claim 1, wherein determining the bounding box comprises:
   identifying a volume of the hematomas based on the plurality of 2D NCCT hematoma images; and
   determining a size of the fixed-size 3D ROI based on the volume.

4. The method of claim 1, wherein generating the hematoma masks comprises:
   identifying, by applying the 2D U-Net CNN, the hematoma based on the plurality of 2D NCCT images of the head; and
   generating the plurality of 2D NCCT hematoma images in which the hematoma is segmented based on the plurality of 2D NCCT images of the head.

5. The method of claim 1, wherein the plurality of 2D NCCT images of the head corresponds to an entire image of the head.

6. The method of claim 5, wherein the fixed-size 3D ROI corresponds to less than the entire image of the head.

7. A device comprising:
   at least one memory configured to store program code;
   at least one processor configured to read the program code and operate as instructed by the program code, the program code including:
   receiving code configured to cause the at least one processor to receive a three dimensional (3D) non-contrast computed tomography (NCCT) image of a head;
   generating code configured to cause the at least one processor to generate a plurality of two dimensional (2D) NCCT images of the head using the 3D NCCT image of the head;
   mask generating code configured to cause the at least one processor to generate, by applying a 2D U-Net convolutional neural network (CNN) on each of the plurality of 2D NCCT images, hematoma masks for the plurality of 2D NCCT hematoma images;
   bounding box code configured to cause the at least one processor to determine a bounding box that contains a hematoma from the hematoma masks such that a center of the hematoma in each of the plurality of 2D NCCT hematoma images coincides;
   determining code configured to cause the at least one processor to determine a fixed-size 3D region of interest (ROI) containing the hematoma from the bounding box;
   extracting code configured to cause the at least one processor to extract the fixed-size 3D ROI from the 3D NCCT image;
   slicing code configured to cause the at least one processor to generate a plurality of 2D NCCT slices of the fixed-size 3D ROI that is extracted;
   HE prediction code configured to cause the at least one processor to predict a hematoma expansion (HE) of the at least one intracranial hemorrhage by inputting each of the plurality of 2D NCCT slices to a 2D NASNet CNN, each of the plurality of 2D NCCT slices being a feature channel of the 2D NASNet CNN, and combining a plurality of outputs of the 2D NASNet CNN to generate an HE prediction score of the at least one intracranial hemorrhage; and providing code configured to cause the at least one processor to provide the HE prediction score.

8. The device of claim 7, wherein the bounding box code comprises:

identifying code configured to cause the at least one processor to identify a volume of the hematoma based on the plurality of 2D NCCT hematoma images; and second determining code configured to cause the at least one processor to determine a size of the fixed-size 3D ROI based on the volume.

9. The device of claim 7, wherein the mask generating code comprises:

identifying code configured to cause the at least one processor to identify, by applying the 2D U-Net CNN, the hematoma based on the plurality of 2D NCCT images of the head; and second generating code configured to cause the at least one processor to generate the plurality of 2D NCCT hematoma images in which the hematoma is segmented based on the plurality of 2D NCCT images of the head.

10. The device of claim 7, wherein the plurality of 2D NCCT images of the head corresponds to an entire image of the head.

11. The device of claim 10, wherein the fixed-size 3D ROI corresponds to less than the entire image of the head.

12. A non-transitory computer-readable medium storing computer code that, when executed by one or more processors, cause the one or more processors to at least:

receive a three dimensional (3D) non-contrast computed tomography (NCCT) image of a head;

generate a plurality of two dimensional (2D) NCCT images of the head using the 3D NCCT image of the head;

generate, by applying a 2D U-Net convolutional neural network (CNN) on each of the plurality of 2D NCCT images, hematoma masks for the plurality of 2D NCCT hematoma images;

determine a bounding box that contains a hematoma from the hematoma masks such that a center of the hematoma in each of the plurality of 2D NCCT hematoma images coincides;

determine a fixed-size 3D region of interest (ROI) containing the hematoma from the bounding box;

extracting the fixed-size 3D ROI from the 3D NCCT image;

generating a plurality of 2D NCCT slices of the fixed-size 3D ROI that is extracted;

predicting a hematoma expansion (HE) of the at least one intracranial hemorrhage by inputting each of the plurality of 2D NCCT slices to a 2D NASNet CNN, each of the plurality of 2D NCCT slices being a feature channel of the 2D NASNet CNN, and combining a plurality of outputs of the 2D NASNet CNN to generate an HE prediction score of the at least one intracranial hemorrhage; and provide the HE prediction score.

13. The non-transitory computer-readable medium of claim 12, wherein to generate the hematoma masks, the computer code is further configured to cause the one or more processors to:

identify, by applying the first 2D CNN, the hematoma based on the plurality of 2D NCCT images of the head; and generate the plurality of 2D NCCT hematoma images in which the hematoma is segmented based on the plurality of 2D NCCT images of the head.

14. The non-transitory computer-readable medium of claim 12, wherein the one or more processors determine the bounding box by at least:

identifying a volume of the hematomas based on the plurality of 2D NCCT hematoma images; and determining a size of the fixed-size 3D ROI based on the volume.

15. The non-transitory computer-readable medium of claim 12, wherein the plurality of 2D NCCT images of the head corresponds to an entire image of the head.

16. The non-transitory computer-readable medium of claim 15, wherein the fixed-size 3D ROI corresponds to less than the entire image of the head.

* * * * *